US011819353B2

(12) United States Patent
Cao et al.

(10) Patent No.: US 11,819,353 B2
(45) Date of Patent: Nov. 21, 2023

(54) CT IMAGING METHOD OF CORONARY ARTERY AND COMPUTER READABLE STORAGE MEDIUM

(71) Applicant: General Electric Company, Schenectady, NY (US)

(72) Inventors: Ximiao Cao, Beijing (CN); Ying Li, Beijing (CN); Li Fang, Beijing (CN)

(73) Assignee: General Electric Company, Schenectady, NY (US)

( * ) Notice: Subject to any disclaimer, the term of this patent is extended or adjusted under 35 U.S.C. 154(b) by 613 days.

(21) Appl. No.: 16/179,416

(22) Filed: Nov. 2, 2018

(65) Prior Publication Data

US 2019/0192102 A1 Jun. 27, 2019

(30) Foreign Application Priority Data

Dec. 27, 2017 (CN) .......................... 201711443775.6

(51) Int. Cl.
| | |
|---|---|
| *A61B 6/00* | (2006.01) |
| *G06T 7/20* | (2017.01) |
| *G06T 11/00* | (2006.01) |
| *G06T 7/00* | (2017.01) |
| *A61B 6/03* | (2006.01) |

(52) U.S. Cl.
CPC ............ *A61B 6/5264* (2013.01); *A61B 6/032* (2013.01); *A61B 6/504* (2013.01); *A61B 6/5205* (2013.01); *A61B 6/5288* (2013.01); *G06T 7/0012* (2013.01); *G06T 7/20* (2013.01); *G06T 11/005* (2013.01); *A61B 6/503* (2013.01); *G06T 2207/10081* (2013.01); *G06T 2207/30048* (2013.01); *G06T 2207/30101* (2013.01); *G06T 2207/30168* (2013.01); *G06T 2211/412* (2013.01)

(58) Field of Classification Search
CPC ... A61B 6/5264; A61B 6/5205; A61B 6/5288; A61B 6/032; A61B 6/504; A61B 6/503; A61B 6/52; A61B 6/03; A61B 6/5258; A61B 6/527; G06T 7/20; G06T 11/005; G06T 7/0012; G06T 2211/412; G06T 2207/10081; G06T 2207/30101; G06T 2207/30168; G06T 2207/30048; G06T 2211/404; G06T 11/006
USPC ......................................................... 600/425
See application file for complete search history.

(56) References Cited

U.S. PATENT DOCUMENTS

| | | | |
|---|---|---|---|
| 2009/0232379 A1* | 9/2009 | Kohler | G06T 11/005 382/131 |
| 2014/0275945 A1* | 9/2014 | Fonte | G06T 7/0012 600/407 |
| 2016/0012613 A1* | 1/2016 | Okerlund | A61B 6/503 382/131 |

\* cited by examiner

*Primary Examiner* — Jason M Ip
*Assistant Examiner* — Renee C Langhals

(57) ABSTRACT

Exemplary embodiments of the present invention provide a CT imaging method of coronary artery and a computer-readable storage medium, the method comprising: generating and outputting a global optimal phase image of a coronary artery; and generating and outputting a local optimal phase image of a particular trunk of the coronary artery based on a trunk selection command.

14 Claims, 4 Drawing Sheets

CT IMAGING METHOD OF CORONARY ARTERY AND COMPUTER READABLE STORAGE MEDIUM

FIELD OF THE INVENTION

The present invention relates to the field of medical imaging, and more particularly to a CT imaging method of coronary artery.

BACKGROUND OF THE INVENTION

When X-ray CT (computing tomography) imaging of a patient's heart, especially the coronary artery is performed, electrocardiographic gating imaging is involved, which includes imaging in synchronization with asystole.

One method of electrocardiographic gating imaging is to collect image data at a particular phase of heart motion and reconstruct the image. The particular phase may be, for example, the phase corresponding to the diastolic phase of heart motion (75% of the phase of an average cardiac cycle). It is usually necessary to observe multiple cardiac cycles and determine the particular phase. However, the heart motion is not completely regular. When the heart rate is not consistent, the particular phase determined is not necessarily accurate. In such a case, image artifacts may easily be created.

Further, in some CT products, the width of the detector can not cover the whole heart, and multiple axis scanning and then merging may be performed, or helical scanning may be performed. In this case, a multi-segment image reconstruction method may be used, which reconstructs an X-ray tomographic image of the heart volume by combining the projected data of the segments obtained in periods corresponding to a plurality of consecutive heartbeats. For example, for a CT product with a 40 mm coverage, three to four cardiac cycles are required, wherein during each cycle, image data at different positions (perspectives) of the heart at the same cardiac motion phase is collected to obtain image date of 3 to 4 segments, and these segments of image data are reconstructed to obtain a complete image of the heart part.

In order to present a user with an image with less artifacts, the prior art also provides the user with the optimal phase of cardiac motion so that the user can collect cardiac image data at this optimal phase. Because the coronary artery includes trunks such as the right coronary artery (RCA), the left anterior descending artery (LAD), and the left circumflex artery (LCX), which are located at different locations in the heart and have different distances from the myocardium, there is also a difference in the degree of synchronization between the motions of these trunks with myocardial motion, and therefore, the optimal phase provided to the user is often better for only some of the trunks, but not for the other trunks, making the images of these other trunks have larger artifacts and do not meet the requirements for a doctor's diagnosis.

BRIEF DESCRIPTION OF THE INVENTION

It is an object of the present invention to provide a CT imaging method of coronary artery capable of providing the optimal image for a particular trunk to meet the requirements for a doctor's diagnosis.

An exemplary embodiment of the present invention provides a CT imaging method of coronary artery, comprising: generating and outputting a global optimal phase image of a coronary artery; and generating and outputting a local optimal phase image of a particular trunk of the coronary artery based on a trunk selection command.

An exemplary embodiment of the present invention provides a CT imaging method of coronary artery, comprising: collecting image data of a coronary artery; obtaining motion indexes of each trunk of the coronary artery at different phases based on the collected image data; determining a local optimal phase for each trunk based on the motion indexes of each trunk at different phases; performing image reconstruction based on the image data at the local optimal phase of a particular trunk to generate a local optimal phase image for the particular trunk.

An exemplary embodiment of the present invention also provides a computer readable storage medium for storing a computer program, which, when installed in a computer system of a CT imaging system, performs the above-described CT imaging method of coronary artery.

Other features and aspects will become apparent from the following detailed description, the drawings, and the claims.

BRIEF DESCRIPTION OF THE DRAWINGS

The invention may be better understood by the description of the exemplary embodiments of the present invention in conjunction with the accompanying drawings, in which.

DETAILED DESCRIPTION OF THE INVENTION

Figure 1:
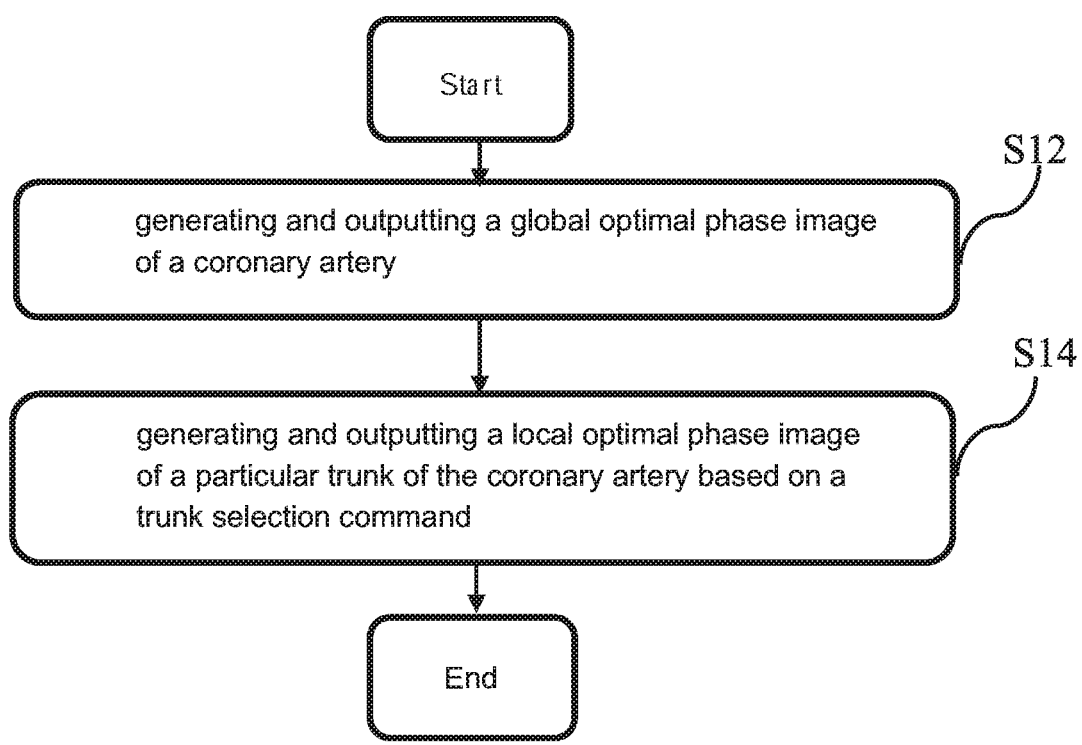
FIG. 1 is a flow chart of an imaging method of coronary artery according to a first embodiment of the present invention.

In the following, specific embodiments of the present invention will be described. It should be noted that, in the detailed description of these embodiments, all features of the actual embodiments may not be described in detail for conciseness and simplicity of the description. It should be understood, in actual implementation of any one of the embodiments, just as in any one engineering project or designing project, in order to achieve the developers' specific goals and in order to meet system-related or business-related restrictions, a variety of concrete decisions are often made, and this varies from one implementation to another. In addition, it should also be understood, although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless otherwise defined, all technical or scientific terms used in the claims and the description should be interpreted in the ordinary sense to one of ordinary skills in the art to which this invention belongs. The terms "first", "second," and the like used in the description and claims of the present invention do not imply any order, quantity, or importance, but are merely used to distinguish between different components. The terms "One", "a/an", and the like do not imply any limitation on the number, but rather means "at least one". The terms "including", "comprising" and the like mean that an element or item appearing before "including" or "comprising" an element or item and its equivalents listed after "including" or "comprising", and does not exclude other elements or items. The terms "connected", "coupled" and the like are not limited to physical or mechanical connections, nor are they limited to direct or indirect connections.

The embodiments of the present invention may be used in CT imaging systems. In one embodiment, the CT imaging system may include a scanning system which includes a gantry that is formed with a cylindrical scanning cavity to receive the patient and a patient table that supports the patient. A bulb and a detector are provided oppositely on the gantry. During the rotation of the gantry, X-rays emitted by the bulb are received by the detector after penetrating human tissues, and the X-rays received by the detector are converted into digital image signals.

The CT imaging system further includes a data collection system and an image reconstruction system, and the data collection system is used for collecting the digital image signals and transmitting the digital image signals as CT raw image data to the image reconstruction system for image reconstruction. The image reconstruction system may be provided on a computer, and the reconstructed image may be output to a display.

The CT imaging system further includes a control system, which may also be provided on the computer, for controlling the scanning system, the data collection system and the image reconstruction system.

FIG. 1 is a flowchart of a CT imaging method of coronary artery according to a first embodiment of the present invention. As shown in FIG. 1, the method includes steps S12 and S14. In step S12, a global optimal phase image of a coronary artery is generated and output; in step S14, a local optimal phase image of a particular trunk of the coronary artery is generated and output based on a trunk selection command.

The coronary artery refers to the artery located in the heart of a human body, and its trunks may include the right coronary artery (RCA), the left anterior descending artery (LAD), the left circumflex artery (LCX), etc.

The global optimal phase image of the above coronary artery refers to the optimal phase of imaging for the entire coronary artery, which may not be the preferred imaging phase for some of these trunks; and the local optimal phase image of a particular trunk refers to the optimal phase of imaging for the particular trunk in the coronary artery. Outputting the global optimal phase image of the coronary artery and then outputting the local optimal phase image of a particular trunk can compensate for the defects that the artifact of the particular trunk in the global optimal phase image may be severe and facilitate a doctor to further perform detailed observation and diagnosis based on the particular trunk.

Figure 2:
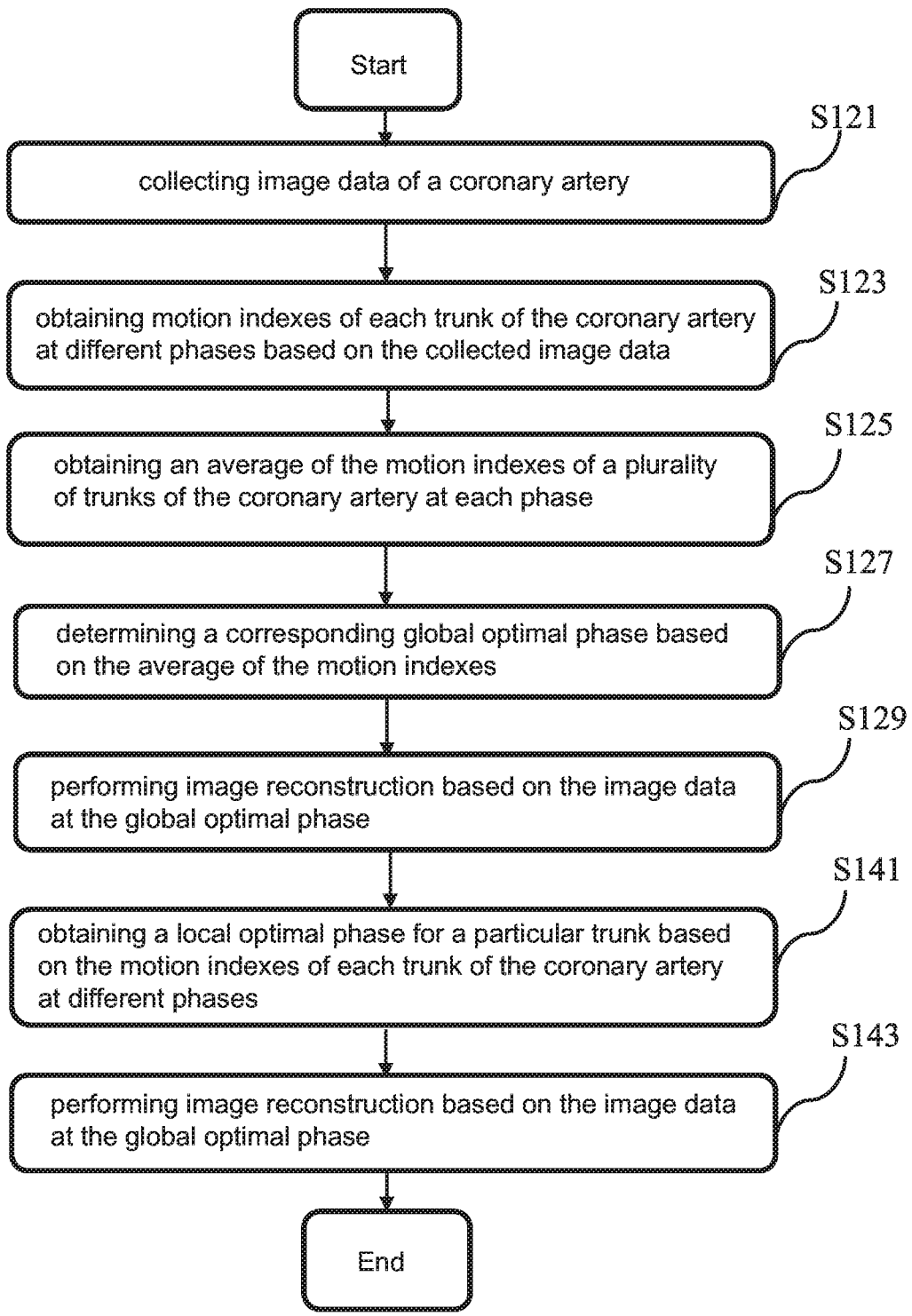
FIG. 2 is a flow chart of a specific embodiment of the CT imaging method of coronary artery in FIG. 1.

FIG. 2 is a flow chart of a specific embodiment of the CT imaging method of coronary artery in FIG. 1. As shown in FIG. 2, in step S12, generating a global optimal phase image of a coronary artery optionally includes steps S121, S123, S125, S127 and S129.

In step S121, image data of the coronary artery is collected. In this step, when the detector width can cover the entire coronary artery, image data of the entire coronary artery is collected at one time.

In step S123, motion indexes of each trunk of the coronary artery at different phases are obtained based on collected image data. In this step, image data at different phases may be analyzed to obtain the motion index of the trunk at the corresponding phase.

The above motion index may refers to a motion quality obtained based on a motion speed, a motion artifact, a motion amplitude, etc. For example, if at a particular phase the motion speed is smaller, the motion amplitude is smaller, and the motion artifact is smaller, it is considered that at the phase the motion is more gentle and the motion quality is higher, otherwise the motion quality is poorer.

All of the above motion speed, motion artifact, motion amplitude, etc may be obtained from analysis of the corresponding image data. For example, image characteristics of different trunks are analyzed based on image data at a particular phase. If the shape of a certain trunk is closer to a circle, or edge sharpness of the trunk is higher, the motion index of the trunk at the phase is higher.

Therefore, motion indexes of each trunk of the coronary artery at different phases can be obtained based on the collected image data.

In step S125, an average of the motion indexes of the plurality of trunks of the coronary artery at each phase is obtained. In this step, for example, an average curve of the motion index curves of RCA, LAD and LCX can be obtained within the phase range of the image data. The horizontal axis of the average curve represents the phase and the vertical axis represents the motion index.

In step S127, the corresponding global optimal phase is determined based on the average of the motion indexes. For example, in the average curve, the phase corresponding to the highest motion index is determined as the global optimal phase.

In step S129, image reconstruction is performed based on the image data at the global optimal phase to obtain a global optimal phase image of the coronary artery.

Optionally, in step S14, generating the optimal phase image of the particular trunk of the coronary artery may particularly include step S141 and step S143.

In step S141, a local optimal phase for the particular trunk is obtained based on the motion indexes of each trunk of the coronary artery at different phases. Since the motion indexes of each trunk at different phases have been obtained in step S123, the corresponding local optimal phase may be mapped according to the motion index of the particular trunk. For example, in the motion index curve of the particular trunk, the phase corresponding to the highest motion index is determined as the local optimal phase of the particular trunk.

In step S143, a local optimal phase image is obtained by performing image reconstruction based on the image data at the local optimal phase. The artifacts of the particular trunk presented in the image are smaller than the global optimal phase image, and the image quality is higher.

Figure 3:
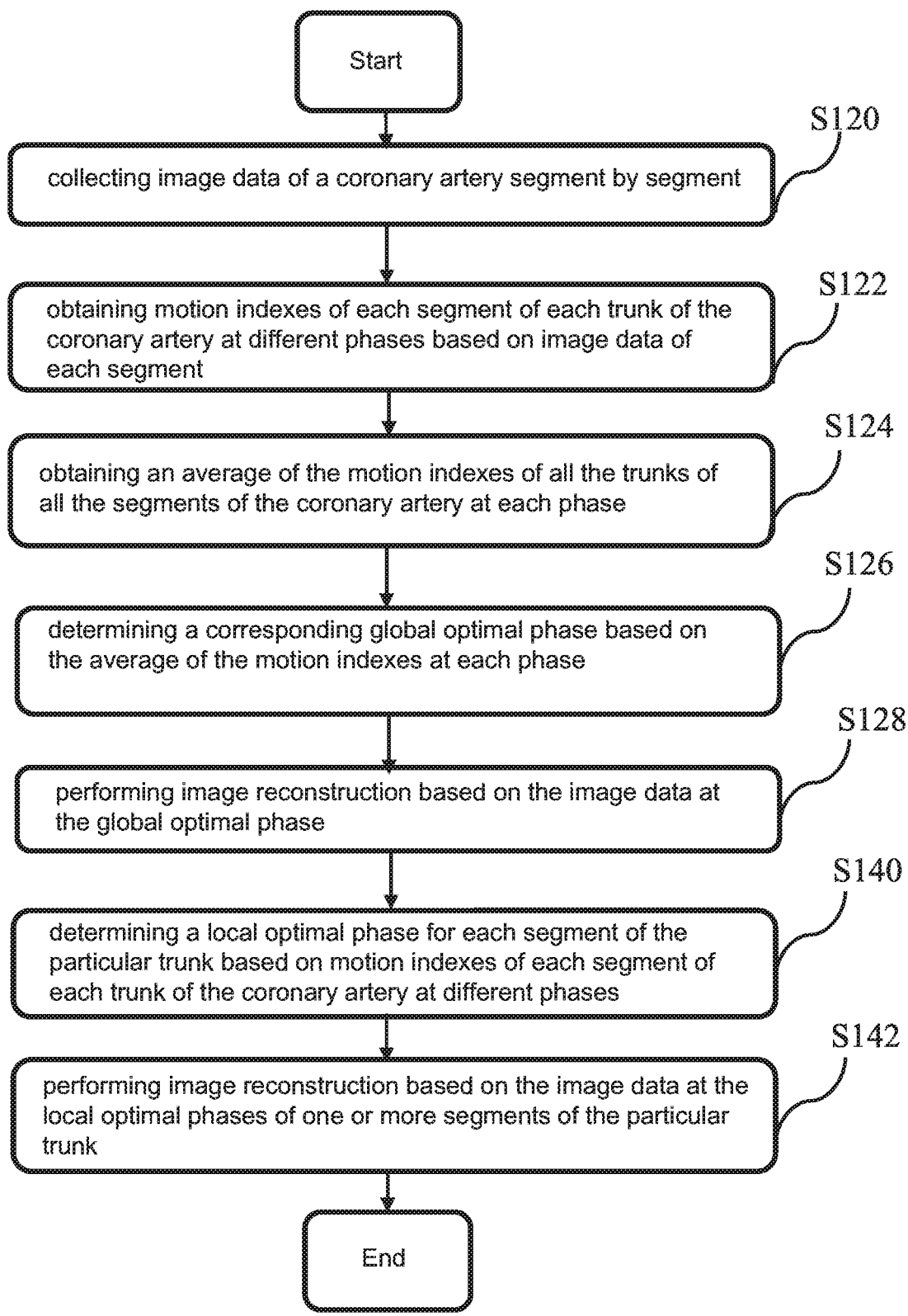
FIG. 3 is a flow chart of a specific embodiment of the CT imaging method of coronary artery in FIG. 1.

FIG. 3 is a flow chart of another specific embodiment of the CT imaging method of coronary artery in FIG. 1. This embodiment is mainly applied to the case of data collection segment by segment. As shown in FIG. 3, in step S12, in this embodiment, generating a global optimal phase image of a coronary artery optionally includes steps S120, S122, S124, S126, and S128.

In step S120, image data of the coronary artery is collected segment by segment. In this step, the purpose of collection segment by segment is to make the final reconstruction image can cover the entire imaging site (the heart and its coronary artery) to obtain a complete image of the imaging site. For example, the coronary artery site may be divided into 4 segments in the Z-direction and image data of the 4 segments may be collected sequentially in the same phase range over 4 cycles of cardiac motion.

In step S122, motion indexes of each segment of each trunk of the coronary artery at different phases are obtained based on each segment's image data. For example, M*N motion index curves may be obtained, where M is the number of segments in the segment-by-segment collection and N is the number of trunks.

In step S124, an average of the motion indexes of all the trunks of all the segments of the coronary artery at each phase is obtained. For example, an average index curve may be obtained by averaging the above M*N motion index curves in phase.

In step S126, the corresponding global optimal phase is determined based on the average of the motion indexes at each phase. For example, the phase at the highest motion index of the average index curve is the global optimal phase.

In step S128, image reconstruction is performed based on the image data at the global optimal phase. For example, image data at the global optimal phase in all image data segments is selected and image reconstruction is performed based on the selected image data.

Further, in step S14, generating a local optimal phase image for a particular trunk of a coronary artery comprises Step 140 and Step 142.

In Step S140, determining a local optimal phase for each segment of the particular trunk based on a motion indexes of each segment of each trunk of the coronary artery at different phases. Since the motion indexes at of each segment of each trunk different phases are already obtained in step S122, the phases corresponding to the highest motion indexes in the M*N motion index curves may be determined as the corresponding M*N local optimal phases.

In Step S142, performing image reconstruction based on the image data at the local optimal phases of one or more segments of the particular trunk. In this step, the selection of the specific trunk and the number of segments may be determined based on the region of interest required by the user. For example, the region of interest may cover all or a part of a certain trunk, or it may cover multiple trunks in multiple segments.

For example, if it is desired to generate the optimal phase image for RCA, four motion index curves for RCA (corresponding to 4 segments respectively, wherein the phases corresponding to the highest motion indexes among the 4 motion index curves may be different) may be found from 12(M*N, M=4, N=3) motion index curves, and 4 optimal phases are found based on the motion index curves of the 4 segments. By image reconstruction performed based on the image data at the 4 optimal phases, the local optimal phase image of all segments of the RCA may be obtained.

According to the above description, in one application of coronary artery imaging, a global optimal phase image may be presented to the user first. If the global optimal phase image can not meet the requirements of the user's diagnosis, for example, there are too many artifacts at a particular trunk (such as RCA) part, which affects diagnosis, then the local optimal phase image for the RCA may be presented. Compared to the global optimal phase image, the local optimal phase image of the RCA part contains less artifacts.

Thus, in step S12, the global optimal phase image of the coronary artery may be presented to the user by default. Meanwhile, in step S14, a local optimal phase image of a particular trunk may be generated based on a trunk selection command, which preferably is generated in response to the user's input. For example, if it is considered by a doctor that a certain trunk contains a large artifact in the default global optimal phase image, then a local optimal phase image of the trunk can be selected and generated by operating on the user interface. Otherwise, if the doctor thinks the default global optimal phase image is enough for diagnosis, this imaging diagnosis may be ended.

Optionally, the CT imaging method of coronary artery in this embodiment may further include the following steps: analyzing the global optimal phase image of the coronary artery; and generating the trunk selection command according to the result of the analysis for the global optimal phase image of the coronary artery.

This approach may be adapted to an automatic imaging process. For example, according to the preset image index, it may be determined whether the image quality of the trunks in the image is good enough. If yes, the coronary artery imaging procedure is ended, and if not, for the particular trunk with insufficient image quality, a local optimal phase image of the particular trunk may be generated and output to a display area for display.

The above analysis of the global optimal phase image of the coronary artery includes the following steps: obtaining the characteristics of the trunks in the global optimal phase image of the coronary artery; and determining the image quality of the trunks as the result of the analysis according to the characteristics of the trunks.

It should be understood by those skilled in the art that the characteristics of the blood vessel may include, for example, shape, edge sharpness, and the like. In the determination, if the shape is closer to a circle and/or the edge sharpness is higher, the image quality is better. On this basis, the result of the analysis may be obtained by comparing these characteristic parameters with a preset threshold.

In addition, this method of analysis can also be applied to the technique described above, i.e., to determine the motion index of the trunks at different phases based on collected image data.

Figure 4:
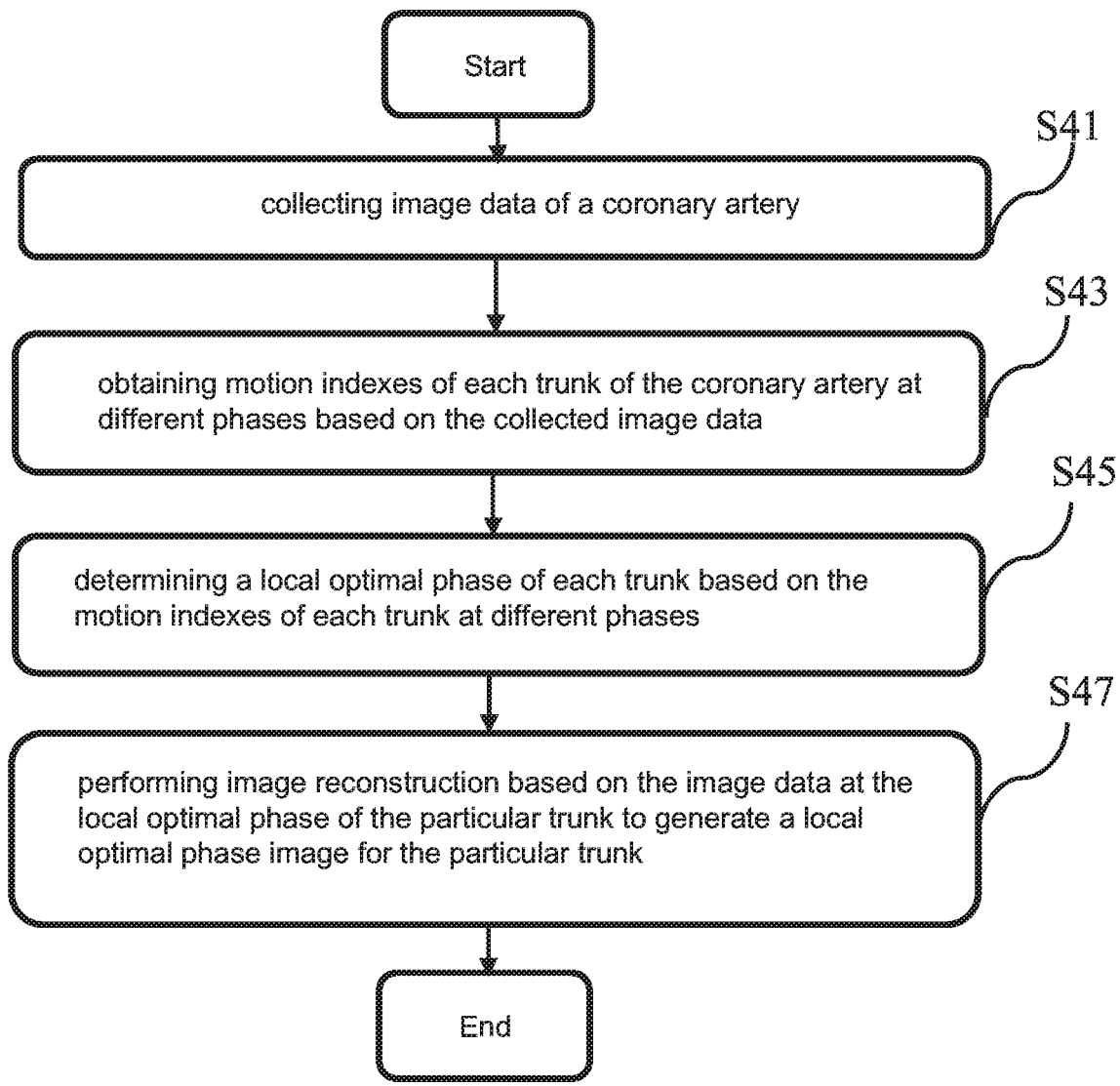
FIG. 4 is a flow chart of an imaging method of coronary artery according to a second embodiment of the present invention.

FIG. 4 is a flow chart of a CT imaging method of coronary artery according to a second embodiment of the present invention. As shown in FIG. 4, the method includes steps S41, S43, S45, and S47.

In step S41, image data of the coronary artery is collected.

In step S43, the motion indexes of each trunk of the coronary artery at different phases are obtained based on the collected image data.

In step S45, the local optimal phases of each trunk are determined based on the motion indexes of each trunk at different phases.

In step S47, image reconstruction is performed based on the image data at the local optimal phase of the particular trunk to generate a local optimal phase image for the particular trunk.

After step S47, the generated local optimal phase image may further be output to a display device for display.

The content of each step in this embodiment has been correspondingly described in the first embodiment, and no further explanation is provided herein.

The imaging method of this embodiment may directly present the optimal phase image of a particular trunk to a user.

Of course, it is also possible to generate and output the global optimal phase image of the coronary artery before generating the optimal phase image of a particular trunk. The phase corresponding to the global optimal phase image of the coronary artery may be the global optimal phase obtained in the manner described in the above embodiment. In other embodiments, the global optimal phase image of the coronary artery may also be generated by other methods.

In this embodiment, step S47 may also be performed based on the trunk selection command to generate a local optimal phase image for a particular trunk. The trunk selection command may be generated according to the result of the analysis for the global optimal phase image of the coronary artery, or may be generated directly by responding to a user's input.

An embodiment of the present invention also provides a computer readable storage medium for storing a computer program, which, when installed in a computer system of a CT imaging system, performs the CT imaging method of coronary artery in the first embodiment above.

Specifically, the computer program may be used to cause the computer system to perform the following operational steps:

Step 1: generating and outputting a global optimal phase image of the coronary artery;

Step 2: generating and outputting a local optimal phase image for a particular trunk of the coronary artery based on the trunk selection command.

wherein, step 1 may include:

Sub-step 1-1, collecting image data of the coronary artery;

Sub-step 1-3: obtaining motion indexes of each trunk of the coronary artery at different phases based on the collected image data;

Sub-step 1-5: obtaining an average of the motion indexes of a plurality of trunks of the coronary artery at each phase;

Sub-step 1-7: determining a corresponding global optimal phase based on the average of the motion indexes;

Sub-step 1-9: performing image reconstruction based on the image data at the global optimal phase.

Step 2 may include:

Sub-step 2-1:

obtaining a local optimal phase for a particular trunk based on motion indexes of each trunk of the coronary artery at different phases;

Sub-step 2-3: performing image reconstruction based on the image data at the local optimal phase.

Optionally, step 1 may further include:

Sub step 1-0, collecting image data of the coronary artery segment by segment;

Sub step 1-2, acquiring motion indexes of each segment of each trunk of the coronary artery at different phases based on image data of each segment;

Sub-step 1-4, obtaining an average of the motion indexes of all the trunks of all the segments of the coronary artery at each phase;

Sub-step 1-6: determining a corresponding global optimal phase based on the average of the motion indexes at each phase;

Sub-step 1-8: performing image reconstruction based on the image data at the global optimal phase.

Step 2 may further include:

Sub step 2-0: determining a local optimal phase for each segment of a particular trunk based on motion indexes of each segment of each trunk of the coronary artery at different phases;

Sub-step 2-2: performing image reconstruction based on the image data at the local optimal phase of one or more segments of the particular trunk.

Further, the computer program may be further configured to execute step 3: generating the trunk selection command by responding to the user's input.

The computer program may also be used to cause the computer system to perform steps 4 and 5 below:

Step 4: analyzing the global optimal phase image of the coronary artery;

Step 5: generating the trunk selection command based on the result of the analysis for the global optimal phase image of the coronary artery.

wherein, step 4 may include:

Sub-step 4-1: obtaining the characteristics of the trunks in the global optimal phase image of the coronary artery;

Sub-step 4-2: determining the image quality of the trunks according to the characteristics of the trunks as the result of the above analysis.

The fourth embodiment of the present invention also provides a computer readable storage medium for storing a computer program, which, when installed in a CT imaging system, performs the CT imaging method of coronary artery in the second embodiment above.

Specifically, the computer program may be used to cause the computer system to perform the following steps:

Step 1, collecting image data of the coronary artery;

Step 2: obtaining motion indexes of each trunk of the coronary artery at different phases based on the collected image data;

Step 3: determining a local optimal phases of each trunk based on the motion indexes of each trunk at different phases;

Step 4: performing image reconstruction based on the image data at the local optimal phase of the particular trunk to generate a local optimal phase image for the particular trunk.

Optionally, before step 4, step 5 may be further included: generating and outputting a global optimal phase image of the coronary artery.

Optionally, step 4 generates a local optimal phase image for a particular trunk by responding to trunk selection command.

Optionally, step 6-1 may further be included between step 4 and step 5: generating the trunk selection command according to the result of the analysis for the global optimal phase image of the coronary artery.

Optionally, step 6-2 may be further included between step 4 and step 5: generating the trunk selection command by responding to the user's input.

In embodiments of the present invention, a local optimal phase image for a particular trunk of a coronary artery may be generated either directly or based on a trunk selection command, allowing a doctor to adequately observe and diagnose the particular trunk, thereby optimizing the imaging procedure and improving efficiency for imaging and diagnosis.

Some exemplary embodiments have been described above, however, it should be understood that various modifications may be made. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementations also fall within the protection scope of the Claims.

We claim:

1. A computed tomography (CT) imaging method of a coronary artery, comprising:

collecting, via a CT imaging system, image data of the coronary artery;

obtaining motion indexes of each trunk of the coronary artery at different phases based on the collected image data;

obtaining an average curve of the motion indexes of a plurality of trunks of the coronary artery, wherein a horizontal axis represents each phase and a vertical axis represents each of the motion index;

determining a corresponding global optimal phase based on the average of the motion indexes, wherein the global optimal phase is the phase corresponding to the highest motion index;

performing image reconstruction based on the image data at the global optimal phase thereby generating a global optimal phase image of the coronary artery;

outputting the global optimal phase image; and generating and outputting a local optimal phase image for a particular trunk of the coronary artery based on a trunk selection command.

2. The method of claim 1, wherein generating the local optimal phase image for the particular trunk of the coronary artery comprises:

obtaining a local optimal phase for the particular trunk based on motion indexes of each trunk of the coronary artery at different phases; and performing image reconstruction based on the image data at the local optimal phase.

3. The method of claim 1, wherein generating the global optimal phase image of the coronary artery comprises:

collecting image data of the coronary artery segment by segment;

acquiring motion indexes of each segment of each trunk of the coronary artery at different phases based on image data of each segment;

obtaining an average of the motion indexes of all the trunks of all the segments of the coronary artery at each phase;

determining a corresponding global optimal phase based on the average of the motion indexes at each phase; and performing image reconstruction based on the image data at the corresponding global optimal phase.

4. The method of claim 3, wherein generating the local optimal phase image for the particular trunk of the coronary artery comprises:

determining a local optimal phase for each segment of the particular trunk based on motion indexes of each segment of each trunk of the coronary artery at different phases; and performing image reconstruction based on the image data at the local optimal phase of one or more segments of the particular trunk.

5. The method of claim 1, wherein the trunk selection command is generated by responding to a user's input.

6. The method of claim 1, further comprising: analyzing the global optimal phase image of the coronary artery, the trunk selection command being generated based on result of an analysis for the global optimal phase image of the coronary artery.

7. The method of claim 6, wherein analyzing the global optimal phase image of the coronary artery comprises:

obtaining characteristics of the trunks in the global optimal phase image of the coronary artery; and determining image quality of the trunks as the result of the analysis according to the characteristics of the trunks.

8. A non-transitory computer-readable storage medium for storing a computer program when installed in a computer system of a computed tomography (CT) imaging system for causing the computer system to:

collect, via the CT imaging system, image data of the coronary artery;

obtain motion indexes of each trunk of the coronary artery at different phases based on the collected image data;

obtain an average curve of the motion indexes of a plurality of trunks of the coronary artery, wherein a horizontal axis represents each phase and a vertical axis represents each of the motion index;

determine a corresponding global optimal phase based on the average of the motion indexes, wherein the global optimal phase is the phase corresponding to the highest motion index;

perform image reconstruction based on the image data at the global optimal phase thereby generating a global optimal phase image of the coronary artery;

output the global optimal phase image; and generate and output a local optimal phase image fora particular trunk of the coronary artery based on a trunk selection command.

9. The non-transitory computer-readable storage medium of claim 8, wherein generating and outputting the local optimal phase image for the particular trunk of the coronary artery comprises:

obtaining a local optimal phase for the particular trunk based on motion indexes of each trunk of the coronary artery at different phases; and performing image reconstruction based on the image data at the local optimal phase.

10. The non-transitory computer-readable storage medium of claim 8, wherein generating the global optimal phase image of the coronary artery comprises:

collecting image data of the coronary artery segment by segment;

acquiring motion indexes of each segment of each trunk of the coronary artery at different phases based on image data of each segment;

obtaining an average of the motion indexes of all the trunks of all the segments of the coronary artery at each phase;

determining a corresponding global optimal phase based on the average of the motion indexes at each phase; and performing image reconstruction based on the image data at the corresponding global optimal phase.

11. The non-transitory computer-readable storage medium of claim 9, wherein generating and outputting the local optimal phase image for the particular trunk of the coronary artery comprises:

determining a local optimal phase for each segment of the particular trunk based on motion indexes of each segment of each trunk of the coronary artery at different phases; and performing image reconstruction based on the image data at the local optimal phase of one or more segments of the particular trunk.

12. The non-transitory computer-readable storage medium of claim 8, wherein the trunk selection command is generated by responding to a user's input.

13. The non-transitory computer-readable storage medium of claim 8, wherein the computer program when installed in the computer system of the CT imaging system further causes the computer system to analyze the global optimal phase image of the coronary artery, the trunk selection command being generated based on result of an analysis for the global optimal phase image of the coronary artery.

14. The non-transitory computer-readable storage medium of claim 13, wherein analyzing the global optimal phase image of the coronary artery comprises:

obtaining characteristics of the trunks in the global optimal phase image of the coronary artery; and determining image quality of the trunks as the result of the analysis according to the characteristics of the trunks.

\* \* \* \* \*